United States Patent [19]

De Lombaert

[11] Patent Number: 5,583,123
[45] Date of Patent: Dec. 10, 1996

[54] CERTAIN TETRAZOLE DERIVATIVES

[75] Inventor: Stéphane De Lombaert, Bernardsville, N.J.

[73] Assignee: Ciba-Geigy Corporation, Tarrytown, N.Y.

[21] Appl. No.: 361,411

[22] Filed: Dec. 22, 1994

[51] Int. Cl.$^6$ .......... A61K 31/675; C07F 9/58; C07F 9/6524; C07F 9/653
[52] U.S. Cl. .......... 514/92; 546/24; 548/119; 548/121; 548/112; 514/82; 514/89
[58] Field of Search .......... 548/112, 119, 548/121; 546/24; 514/82, 92, 89

[56] References Cited

U.S. PATENT DOCUMENTS

| | | | |
|---|---|---|---|
| 5,155,100 | 10/1992 | Erion et al. | 514/119 |
| 5,250,522 | 10/1993 | DeLombaert | 514/114 |
| 5,273,990 | 12/1993 | DeLombaert | 514/381 |

FOREIGN PATENT DOCUMENTS

| | | |
|---|---|---|
| 0054862 | 11/1985 | European Pat. Off. . |
| 0618224 | 5/1994 | European Pat. Off. . |
| 0623625 | 11/1994 | European Pat. Off. . |
| 9311154 | 6/1993 | WIPO . |
| 9405677 | 3/1994 | WIPO . |

OTHER PUBLICATIONS

Trapani et al., J. Cardiovasc. Pharmacol. 1995, vol. 26, (Suppl. 3), pp. 569–571.
FASB Journal, Abstracts, Endothelin/Endothelin Receptors, Mar. 15, 1994.
Research Communications in Chemical Pathology and Pharmacology, vol. 52, No. 1, Apr. 1986.
Biochemical & Biophysical Research Communications, vol. 204, No. 1, 1994.
Bioorganic & Medicinal Chemistry Letters, vol. No. 10, pp. 1257–1262, 1994.

*Primary Examiner*—David B. Springer
*Attorney, Agent, or Firm*—Norbert Gruenfeld

[57] ABSTRACT

The present invention relates to the phosphono-alkylamino-substituted tetrazole derivatives of formula I

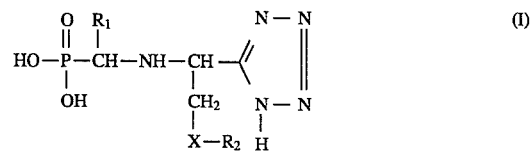

and tautomers thereof wherein $R_1$ is (carbocyclic or heterocyclic) aryl-$C_1$–$C_4$-alkyl; X is phenylene, phenylene substituted by lower alkoxy, lower-alkyl, halogen or trifluoromethyl or $X_1$ is ethynylene; $R_2$ is carbocyclic or heterocyclic aryl; pharmaceutically acceptable mono- or di-ester derivatives thereof in which one or both of the acidic hydroxy groups of the phosphono functional group are esterified in form of a pharmaceutically acceptable mono- or di-ester, and pharmaceutically acceptable salts thereof; pharmaceutical compositions comprising said compounds; methods for preparation of said compounds and for the preparation of intermediates; and methods of treating disorders in mammals which are responsive to the inhibition of endothelin-converting enzyme by administration of said compounds to mammals in need of such treatment.

20 Claims, No Drawings

CERTAIN TETRAZOLE DERIVATIVES

SUMMARY OF THE INVENTION

Endothelin, a potent biological mediator in mammals, e.g. as a vasoconstrictor, is generated in mammals through enzymatic cleavage of the biologically inert big endothelin by endothelin-converting enzyme.

The aim of the present invention is to provide novel phosphonoalkylamino-substituted tetrazole derivatives described below which are useful as endothelin-converting enzyme (ECE) inhibitors in mammals.

The compounds of the invention thus inhibit the formation of endothelin, reduce the plasma and tissue levels of endothelin and inhibit the biological affects of endothelin activity in mammals. The compounds of the invention are thus also useful for the treatment of endothelin dependent conditions and diseases, e.g. cardiovascular disorders such as essential hypertension, heart failure, pulmonary hypertension, cerebral ischemia, renal failure, atherosclerosis, cerebral vasospasm, arterial hypertrophy, restenosis, and myocardial infarction, also respiratory disorders such as bronchial asthma, and gastrointestinal disorders such as inflammatory bowel disease.

DETAILED DESCRIPTION OF THE INVENTION

The present invention relates to the phosphono-alkylamino-substituted tetrazole derivatives of formula I

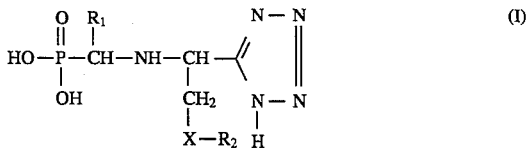

and tautomers thereof wherein $R_1$ is (carbocyclic or heterocyclic) aryl-$C_1$-$C_4$-alkyl; X is phenylene, phenylene substituted by lower alkoxy, lower-alkyl, halogen or trifluoromethyl or X is ethynylene; $R_2$ is carbocyclic or heterocyclic aryl; pharmaceutically acceptable mono- or di-ester derivatives thereof in which one or both of the acidic hydroxy groups of the phosphono functional group are esterified in form of a pharmaceutically acceptable mono- or di-ester, and pharmaceutically acceptable salts thereof; pharmaceutical compositions comprising said compounds; methods for preparation of said compounds and for the preparation of intermediates; and methods of treating disorders in mammals which are responsive to the inhibition of endothelin-converting enzyme by administration of said compounds to mammals in need of such treatment.

Compounds of formula I and derivatives thereof, depending on the nature of substituents, possess two or more asymmetric carbon atoms. The resulting diastereoisomers and optical antipodes are encompassed by the instant invention.

The tetrazoles can exist in tautomeric forms or mixtures thereof, in which the hydrogen can be located on any of the ring nitrogen: such are also encompassed by the instant invention.

Pharmaceutically acceptable ester derivatives are preferably prodrug ester derivatives, such being convertible by solvolysis or under physiological conditions to the free phosphonic acids of formula I, e.g. the phosphonic acid esters illustrated in European Patent application No. 481,214 as prodrugs of phosphonate nucleotide analogs.

Examples of such phosphonic acid esters are aryl, tetrahydronaphthyl and indanyl esters; α-acyloxymethyl esters optionally substituted by lower alkyl, by $C_5$-$C_7$-cycloalkyl, by aryl or by aryl-lower alkyl; lower alkyl and aryl-lower alkyl esters, each substituted on the α-carbon by carboxy, esterified or amidated carboxy, or by trichloromethyl.

A preferred embodiment of the invention relates to the compounds of formula II

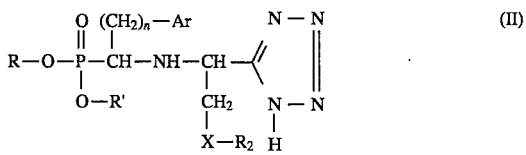

and tautomers thereof wherein R and R' represent independently hydrogen, carbocyclic aryl, 6-tetrahydronaphthyl, 5-indanyl, α-(trichloromethyl, carboxyl, esterified carboxyl or amidated carboxyl)-substituted-(lower alkyl or aryl-lower alkyl), acyloxymethyl optionally monosubstituted on methyl carbon by lower alkyl, by $C_5$-$C_7$-cycloalkyl, by aryl or by aryl-lower alkyl; Ar represents phenyl, or phenyl substituted by hydroxy, lower alkyl, lower alkoxy, halogen or trifluoromethyl; or Ar represents naphthyl, indolyl, benzofuranyl, benzothienyl, quinolinyl, isoquinolinyl or benzoxazolyl, each optionally substituted by hydroxy, lower alkyl or lower alkoxy; n represents the integer 1, 2 or 3; X represents phenylene or ethynylene; $R_2$ represents naphthyl, phenyl or phenyl substituted by lower alkyl or lower alkoxy; or $R_2$ represents pyridyl, thienyl, furanyl, isoxazolyl, triazolyl, tetrazolyl or pyrrolyl each unsubstituted or substituted by lower alkyl; and pharmaceutically acceptable salts thereof.

Particularly preferred are said compounds of formula II and tautomers thereof wherein R and R' independently represent hydrogen, α-(carboxy, lower alkoxycarbonyl, carbocyclic arylmethoxycarbonyl, aminocarbonyl or mono- or di-lower alkylaminocarbonyl)-substituted-(lower alkyl or carbocyclic aryl-lower alkyl), 5-indanyl, phenyl, or phenyl substituted by one, two or three substituents selected from lower alkyl, halogen, lower alkoxy, lower alkanoylamino, trifluoromethyl, lower alkyl-(thio, sulfinyl or sulfonyl), and lower alkoxycarbonyl.

Advantageously, R and R' are either identical, or one of R and R' represents hydrogen while the other of R and R' has any of the other meanings as defined herein.

A particular preferred embodiment of the invention relates to the above compounds having the (S)-configuration at the asymmetric carbon adjacent to the tetrazole ring. Preferred is also the more biologically active of the two diastereomers with the S-configuration at the asymmetric carbon adjacent to the tetrazole ring and either the S or R configuration at the carbon adjacent to the phosphono grouping.

Preferred embodiments relate to the compounds of formula I wherein $R_1$ represents 1-naphthyl-($C_1$-$C_4$)-alkyl, X represents 1,4-phenylene and $R_2$ represents phenyl; the S,S or R,S-diastereomers thereof; pharmaceutically acceptable salts thereof; and prodrug esters thereof.

Similarly preferred are the compounds of formula II wherein n represents 1, 2 or 3; Ar represents 1-naphthyl; X represents 1,4-phenylene; $R_2$ represents phenyl; R and R' represent hydrogen or phenyl; the S,S or R,S-diastereomers thereof; pharmaceutically acceptable salts thereof; and prodrug esters thereof.

The definitions used herein, unless denoted otherwise, have the following meanings within the scope of the present invention.

Carbocyclic aryl represents preferably monocyclic carbocyclic aryl or optionally substituted naphthyl.

Monocyclic carbocyclic aryl represents optionally substituted phenyl, being preferably phenyl or phenyl substituted by one to three substituents, such being advantageously lower alkyl, hydroxy, lower alkoxy, lower alkanoyloxy, halogen, cyano, trifluoromethyl, lower alkanoylamino, lower alkyl-(thio, sulfinyl or sulfonyl) or lower alkoxycarbonyl.

Optionally substituted naphthyl (also called herein naphthalenyl) represents 1- or 2-naphthyl or 1- or 2-naphthyl preferably substituted by lower alkyl, lower alkoxy or halogen.

Heterocyclic aryl represents monocyclic or bicylic heterocylic aryl.

Monocyclic heterocyclic aryl represents preferably optionally substituted thienyl, furanyl, pyridyl, pyrrolyl, isoxazolyl or triazolyl, or tetrazolyl.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl.

Optionally substituted pyrrolyl is 1-, 2- or 3-pyrrolyl or 1-, 2- or 3-pyrrolyl optionally substituted by lower alkyl.

Optionally substituted isoxazolyl is 3-, 4- or 5-isoxazolyl optionally substituted by lower alkyl.

Optionally substituted triazolyl is preferably 3- or 5-(1,2,4)-triazolyl or 3- or 5-(1,2,4)-triazolyl optionally substituted by lower alkyl.

Tetrazolyl is 1- or 5-tetrazolyl, preferably 1-tetrazolyl.

Bicyclic heterocyclic aryl represents preferably optionally substituted indolyl, benzofuranyl, benzothienyl, benzoxazolyl, quinolinyl or isoquinolinolyl.

Optionally substituted indolyl represents preferably 3-indolyl or 3-indolyl substituted by lower alkyl, lower alkoxy or hydroxy.

Optionally substituted benzofuranyl represents preferably 2- or 3-benzofuranyl or 3-benzofuranyl substituted by lower alkyl, hydroxy or lower alkoxy.

Optionally substituted benzothienyl represents preferably 3-benzothienyl or 3-benzothienyl substituted by lower alkyl, hydroxy or lower alkoxy.

Optionally substituted benzoxazolyl represents preferably 2-benzoxazolyl or 2-benzoxazolyl substituted by lower alkyl, hydroxy or lower alkoxy.

Optionally substituted quinolinyl represents preferably 2-, 3- or 4-quinolinyl or 2-, 3- or 4-quinolinyl substituted by lower alkyl.

Optionally substituted isoquinolinyl represents preferably 1-, 3- or 4-isoquinolinyl or 1-, 3- or 4-isoquinolyl substituted by lower alkyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents for example ethyl, propyl, butyl or advantageously methyl.

A lower alkoxy group preferably contains 1–4 carbon atoms and represents for example methoxy, propoxy, isopropoxy or advantageously ethoxy.

Aryl-lower alkyl as such, unless denoted otherwise, is advantageously benzyl or phenethyl optionally substituted by one or two of lower alkyl, lower alkoxy, hydroxy, lower alkanoyloxy, halogen or trifluoromethyl.

The term $C_5$–$C_7$-cycloalkyl represents a saturated cyclic hydrocarbon radical which preferably contains 5 to 7 ring carbons and is, preferably cyclopentyl or cyclohexyl.

The term cycloalkyl(lower)alkyl represents preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

Phenylene is 1,2-, 1,3- or 1,4-phenylene, advantageously 1,4-phenylene.

Esterified carboxy represents preferably lower alkoxycarbonyl, or aryl-lower alkoxycarbonyl.

Amidated carboxy represents preferably aminocarbonyl, mono- or di-lower alkylaminocarbonyl.

Amino-lower alkyl represents preferably amino-(ethyl, propyl or butyl), particularly omega-amino-(ethyl, propyl or butyl).

A di-lower alkylamino group preferably contains 1–4 carbon atoms in each lower alkyl portion and represents, for example, N,N-dimethylamino, N-methyl-N-ethylamino and advantageously N,N-diethylamino.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

An aryl-lower alkoxycarbonyl group is preferably (monocyclic carbocyclic or heterocyclic)-substituted-lower alkoxy-carbonyl, such as benzyloxycarbonyl.

Lower alkoxycarbonyl-lower alkoxy represents advantageously e.g. 1-(ethoxycarbonyl)ethoxy or ethoxycarbonylmethoxy.

Di(lower)alkylamino-lower alkoxy advantageously represents diethylaminoethoxy.

Halogen (halo) preferably represents fluoro or chloro, but may also be bromo or iodo.

Lower alkanoyl is preferably acetyl, propionyl, butyryl, or pivaloyl.

Lower alkanoyloxy is preferably acetoxy, pivaloyloxy or propionyloxy.

Acylamino represents preferably lower alkanoylamino, aroylamino, or aryl-lower alkoxycarbonylamino such as benzyloxycarbonylamino.

Lower alkanoylamino is preferably acetamido or propionamido.

Aroyl is preferably benzoyl or benzoyl substituted on the benzene ring by lower alkyl, lower alkoxy, halogen or trifluoromethyl.

Acyl represents preferably lower alkanoyl, carbocyclic aryl-lower alkanoyl, aroyl, lower alkoxycarbonyl or aryl-lower alkoxycarbonyl, advantageously lower alkanoyl. Lower alkoxycarbonyl for acyl is preferably t-butoxycarbonyl (abbreviated t-BOC). Aryl-lower alkoxycarbonyl for acyl is preferably benzyloxycarbonyl (abbreviated CBZ).

Phosphono esterified in the form of a pharmaceutically acceptable ester represents mono- or di-esters thereof, preferably phosphono derivatized as mono- or di-prodrug esters such as mono- or di-carbocyclic arylphosphono, e.g. mono- or di-phenylphosphono; mono- or di-5-indanylphosphono; mono- or di-acyloxymethylphosphono optionally substituted on methyl by lower-alkyl, by $C_5$–$C_7$-cycloalkyl, by aryl (e.g. phenyl) or by aryl-lower alkyl (e.g. benzyl), and wherein acyloxy represents lower-alkanoyloxy, $C_5$–$C_7$-cycloalkanoyloxy, carbocyclic aroyloxy or carbocyclic aryl-lower alkanoyloxy; as mono- or di-(α-lower alkoxycarbonyl-lower alkyl)phosphono; as mono- or di-(α-di-lower alkylaminocarbonyl-lower alkyl)phosphono; also as mono- or di-(α-trichloromethyl-lower alkyl)phosphono.

Phosphono esterified as a mono- or di-prodrug ester relates to a pharmaceutically acceptable mono- or di-phosphono ester that may be convertible by solvolysis or under physiological conditions to phosphono (the free phosphonic acid).

Pharmaceutically acceptable salts are pharmaceutically acceptable acid addition salts for any basic compounds of the invention or salts derived from pharmaceutically acceptable bases for any acidic compounds of the invention.

Pharmaceutically acceptable salts of basic compounds of the invention are acid addition salts, which are preferably such of therapeutically acceptable inorganic or organic acids, such as strong mineral acids, for example hydrohalic, e.g. hydrochloric or hydro-bromic acid, sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, 1,2-ethanedisulfonic acid, benzenesulfonic, p-toluenesulfonic, naphthalenesulfonic, sulfanilic, cyclohexylsulfamic acid, or ascorbic acid.

Pharmaceutically acceptable salts of the acidic compounds of the invention, e.g. those having a free phosphono hydroxyl group are salts formed with pharmaceutically acceptable bases, e.g. alkali metal salts (e.g. sodium, potassium salts), alkaline earth metal salts (e.g. magnesium, calcium salts), amine salts (e.g. ethanolamine, diethanolamine, triethanolamine, tromethamine salts).

The novel compounds of the invention are pharmacologically potent endothelin converting enzyme inhibitors which inhibit the formation of endothelin in mammals. They thus inhibit the biological effects of endothelin in mammals.

The compounds of the invention are thus particularly useful in mammals e.g. as cardiovascular agents for the treatment of e.g. hypertension and heart failure and as pulmonary agents for the treatment of bronchial asthma.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-5}$ molar and $10^{-9}$ molar concentrations. The dosage in vivo may range depending on the route of administration, between about 0.1 and 50 mg/kg, advantageously between about 1.0 and 25 mg/kg.

The in vitro inhibition of endothelin-converting enzyme can be determined as follows:

The test compound is dissolved in dimethyl sulfoxide or 0.25M sodium bicarbonate solution, and the solution is diluted with pH 7.4 buffer to the desired concentration.

Endothelin converting enzyme (ECE) is partially purified from porcine primary aortic endothelial cells by DE52 anion exchange column chromatrography and its activity is quantified by radioimmunoassay as described in Anal. Biochem. 213, 434–436 (1993). The ECE inhibition can be determined as described in Biochem. Mol. Biol. Int. 31, (5), 861–867 (1993), by radioimmunoassay to measure ET-1 formed from big ET-1.

In vitro testing is most appropriate for the free phosphonic acids of the invention.

Illustrative of the invention, the compound of example 1 (a) demonstrates an $IC_{50}$ of about 370 nM in the in vitro assay for endothelin converting enzyme inhibition.

Endothelin converting enzyme inhibition can also be determined in vivo by measuring the inhibition of big ET-1-induced pressor response in the anesthesized rat. The effect of the inhibitors on the pressor response resulting from big ET-1 challenge is measured in Sprague-Dawley rats as described in Biochem. Mol. Biol. Int. 31, (5), 861–867 (1993). Results are expressed as percent inhibition of big ET-1-induced pressor response as compared to vehicle.

ECE inhibition can also be determined in vivo by measuring the inhibition big ET-1 induced pressor response in conscious spontaneously hypertensive rats (SHR), e.g. as described in Biochem. Biophys. Res. Communic. 204, 407–412 (1994).

Male SHR (16–18 weeks of age) are administered either test compound or vehicle (1M $NaHCO_3$) via an osmotic minipump implanted subcutaneously. On day 5 femoral arterial and venous catheters are placed in anesthetized rats for the measurement of MAP (mean arterial pressure) and for test compound administration, respectively. After a 48 hour recovery period, MAP is recorded (day 7) through the arterial catheter connected to a pressure transducer. Blood pressure and heart rate are allowed to stabilize for 30 minutes before ganglion blockade is performed using chlorisondamine (10/kg i.v.). Approximately 15 minutes later, a bolus dose of big ET-1 (0.25 nmol/kg i.v.) is administered to both vehicle- and test compound treated rats. The change in blood pressure in response to big ET-1 is then compared between the two groups of rats at 1, 5, 10, 15, 30 and 60 min after dosing using a two-way ANOVA.

Bronchial activity can be determined by measuring the effect in a model of ET-1 induced bronchoconstriction.

The compound of the invention may also possess neutral endopeptidase inhibitory activity. Tests for determination thereof are described in U.S. Pat. No. 5,273,990 issued Dec. 28, 1993 which is incorporated herein by reference.

The compounds of the invention can be prepared using processes described and illustrated below, e.g. by (a) reacting a compound of the formula

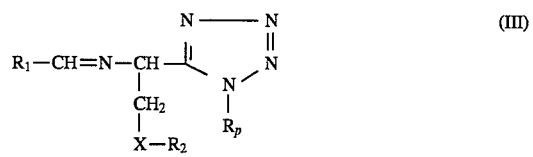

wherein $R_1$, $R_2$ and X have meaning as defined hereinabove, and $R_p$ represents a protecting group; with a compound of the formula

or

or an alkali metal salt of a compound of formula IVa, wherein $R_a$ and $R_a'$ have meaning as defined herein for R and R', except that $R_a$ and $R_a'$ do not represent hydrogen, and $R_a$ and $R_a'$ in addition represent lower alkyl or aryl-lower alkyl; $R_a''$ has meanings of $R_a$ and $R_a'$ above and may further preferentially represent trialkylsilyl, e.g. trimethylsilyl; and then removing the protecting group $R_p$; or (b) condensing a protected α-(aminoalkyl)tetrazole of the formula

wherein $R_2$ and X have meaning as defined hereinabove and $R_p$ is a protecting group; with a compound of the formula

wherein $R_1$ has meaning as defined hereinabove and $R_b$ and $R_b'$ represent lower alkyl or aryl-lower alkyl, e.g. optionally substituted benzyl, and Z represents a leaving group, e.g. a reactive esterified hydroxyl group, such as trifluoromethylsulfonyloxy; and removing the protecting group $R_p$; or (c) reacting an amide of the formula

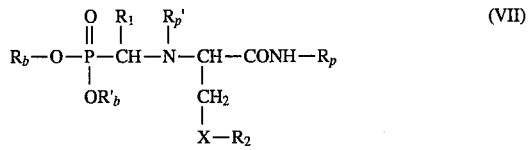

wherein $R_1$, $R_2$ and X have meaning as defined above; $R_b$ and $R_b'$ represent lower alkyl or aryl-lower alkyl, e.g. optionally substituted benzyl; and $R_p$ and $R_p'$ represent a protecting group; with a di-lower alkyl azodicarboxylate and a triaryl phosphine (e.g. triphenylphosphine), with hydrazoic acid (preferably generated in situ) or a reactive azide, such as trimethylsilyl azide, or with triflic anhydride and an azide salt (e.g. sodium azide) according to Synthesis 767 (1993), to obtain a compound of the formula

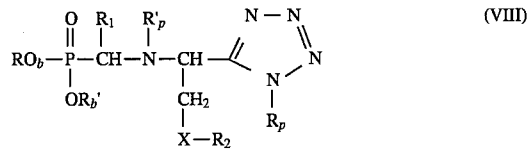

wherein $R_1$, $R_2$, X, $R_b$, $R_b'$, $R_p$ and $R_p'$ have meaning as defined above; and removing the protecting groups $R_p$ and $R_p'$; or (d) condensing a compound of the formula

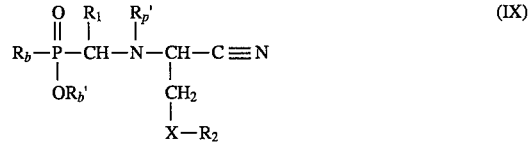

wherein $R_1$, $R_2$, X, $R_p'$, $R_b$ and $R_b'$ have meaning as defined hereinabove, with hydrazoic acid (preferably generated in situ) or a reactive azide derivative, such as a trialkyl silyl azide or a trialkyltin azide, and liberating the free tetrazole from the resulting trialkylsilyl or trialkyltin substituted tetrazole by e.g. acid hydrolysis; and removing the protecting group $R_p'$;

(e) and converting any compound obtained in any said process, in which any of $R_a$, $R_b$, $R_a'$ and $R_b'$ represent lower alkyl or aryl-lower alkyl, to a corresponding product of the invention in which such have meaning as defined for R and R' in formula II; and in above said processes, if temporarily protecting any interfering reactive group(s), removing said protecting group(s), and then isolating the resulting compound of the invention; and, if desired, converting any resulting compound of the invention into another compound of the invention; and/or, if desired, converting a free phosphonic acid function into a pharmaceutically acceptable ester derivative, or converting a resulting ester into the free acid or into another ester derivative; and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate into the optical antipodes.

In starting compounds and intermediates which are converted to the compounds of the invention in a manner described herein, functional groups present, such as phosphonyl, amino and hydroxy groups, are optionally protected by conventional protecting groups that are common in preparative organic chemistry. Protected phosphonyl, amino and hydroxy groups are those that can be converted under mild conditions into free phosphonyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (phosphonyl, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. 1973, T. W. Greene and P. G. M. Wuts, "Protective Groups in Organic Synthesis", Wiley, New York 1991, and also in "The Peptides", Vol. I, Schroeder and Luebke, Academic Press, London, N.Y., 1965.

A tetrazole protecting group $R_p$ is a group which can be introduced in form of an amide and such is e.g. cyanoethyl, p-nitrophenylethyl, lower alkoxycarbonylethyl, benzyl, p-methoxybenzyl, phenylsulfonylethyl and the like. Such ethyl substituted tetrazole protecting groups can be removed e.g. by a retro-Michael deblocking reaction with a base such as DBN (1,5-diazabicyclo[4.3.0]non-5-ene), DBU (1,8-diazabicyclo[5.4.0]undec-7-ene), an amidine, an alkali metal hydroxide, carbonate or alkoxide, e.g. potassium carbonate, sodium or potassium hydroxide, potassium t-butoxide, sodium methoxide in an inert solvent.

The amino protecting group $R_p'$ represents preferably an acyl protecting group such as t-butoxycarbonyl or benzyloxycarbonyl.

A reactive esterified hydroxyl group, such as Z in a compound of the formula VI or XVI, is a hydroxyl group esterified by a strong inorganic or organic acid. Corresponding Z groups are in particular halo, for example chloro, bromo or preferably iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The preparation of compounds of the invention according to process (a), i.e. the condensation of an imine derivative of formula III with a silyl phosphite diester of formula IV is carried out in an inert solvent such as toluene or benzene, preferably at elevated temperature, to yield e.g. a compound of formula X

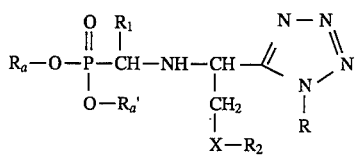 (X)

wherein $R_1$, X, $R_2$, $R_p$, $R_a$ and $R_a'$ have meaning as defined above.

The silyl phosphite diesters of formula IV are known or can be prepared in situ by treatment of the corresponding compound of formula IVa

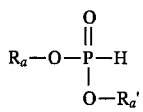 (IVa)

with a trialkyl silyl chloride, such as trimethylsilyl chloride according to Tetrahedrom 46, 7175 (1990). The compounds of formula IVa are known or can be prepared according to methods in the literature, e.g. U.S. Pat. No. 3,329,742 for the preparation of diaryl phosphites, by reaction of the alcohol corresponding to $R_a$ and $R_a'$ with phosphorus trichloride.

Unsymmetrical diesters of formula IVa can be prepared by first treating a symmetrical diester, e.g. dibenzyl phosphite, with aqueous base, e.g. aqueous tetramethyl ammonium hydroxide, to obtain a monoester, e.g. monobenzyl phosphite. This can be treated e.g. with an appropriate alkyl halide corresponding to R or R' in formula II, for example an α-alkoxycarbonylalkyl bromide, to obtain a compound of formula IVa wherein $R_a$ is benzyl and $R_a'$ is α-alkoxycarbonylalkyl. Alternatively, monobenzyl phosphite can first be converted to e.g. a mixed anhydride (e.g. with pivaloyl chloride) which is then reacted with an appropriate alcohol or phenol corresponding to R or R' in formula II to obtain a corresponding unsymmetrical diester of formula IVa. The resulting condensation product of formula X wherein either $R_a$ or $R_a'$ represents benzyl can then be converted to a compound of formula II wherein either R or R' represents hydrogen by selective catalytic hydrogenolysis of the benzyl substituent.

As to the imine compounds of formula III, such can be prepared starting from the N-acyl amino acid of the formula XI

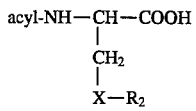 (XI)

wherein $R_2$ and X have meaning as defined herein and acyl represents an easily removable acyl protecting group, as illustrated below.

For example, an N-acylbiarylalanine ester, e.g. N-t-butoxycarbonyl-4-biphenylalanine methyl ester, is selectively hydrolyzed with dilute base to the corresponding N-acylbiarylalanine, e.g. N-t-butoxycarbonyl-4-biphenylalanine. The carboxylic acid is converted e.g. to a mixed anhydride which is then treated with an amine of the formula XII

 $NH_2-R_p$ (XII)

wherein $R_p$ has meaning as defined herein, and the resulting amide is then treated under conditions of tetrazole formations, e.g. under conditions described in Tetrahedron Letters 1979, 491 and J. Org. Chem. 56 2395 (1991), such as by reaction with an azide such as trimethylsilyl azide upon amide activation, with e.g. diethyl azodicarboxylate and triphenylphosphine, to obtain a protected tetrazole intermediate which is then N-deacylated to the intermediate of formula V

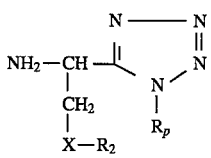 (V)

wherein $R_2$, X and $R_p$ have meaning as defined herein.

The imines (Schiff bases) of formula III are then prepared in situ by condensation of a tetrazole of formula V, according to the general known process for the synthesis of imine derivatives (Schiff bases), with an aldehyde of the formula $R_1$—CHO wherein $R_1$ has meaning as defined herein.

The α-amino acid corresponding to starting materials of formula XI are either known in the art or can be prepared according to methods reported in the art.

As to the preparation of the amino acid starting materials in optically active form, such can be prepared e.g. by resolution or by one of the following methods, as illustrated for biphenylalanines:

(1) Adapting a method described in J. Am. Chem. Soc. 1991, 113, 9276 a biarylmethanol, e.g. 4-biphenylylmethanol, is converted to a reactive derivative, e.g. the bromide, which is then condensed with an N-acyl derivative of 2,3-diphenyl-6-oxomorpholine, e.g. the N-carbobenzyloxy-(2R,3S)-isomer, in the presence of a strong base such as sodium bis-trimethylsilylamide, to yield e.g. N-carbobenzyloxy-2(R), 3(S), 5(S)-6-oxo-2,3-diphenyl-5-(4-biphenylylmethyl)-morpholine. Catalytic hydrogenolysis, e.g. using hydrogen and palladium on charcoal as catalyst, yields the optically active (S)-(+)-4-biphenylalanine.

(2) Alternatively, using the Pd (O)-catalyzed cross-coupling reaction described by W. Shieh et al, J. Organic Chemistry, 57, 379 (1992) the substantially optically pure chiral biarylalanines, of the formula

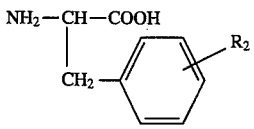

or the N-acyl and/or carboxy ester derivatives thereof wherein $R_2$ represents aryl as defined hereinabove, can be prepared by: condensing a reactive esterified optically active tyrosine derivative of the formula

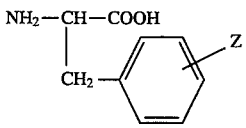

wherein the amino and carboxy groups are in protected form (as N-acyl and esterified carboxy ester derivatives), and Z represents reactive esterified hydroxy (advantageously trifluoromethylsulfonyloxy) with an aryl boronic acid in which aryl corresponds to $R_2$ as defined above, in the presence of a palladium (O) catalyst, in particular tetrakis(triphenylphosphine)palladium (O), and in the presence of an anhydrous base (such as an alkali metal carbonate), in an inert solvent (such as xylene or toluene) at an elevated temperature ranging from about 50° to 150° C., and removing any protecting groups as required.

For example, N-t-butoxycarbonyl-tyrosine methyl ester is first converted to N-t-butoxycarbonyl-4-trifluoromethylsulfonyloxy-phenylalanine methyl ester (N-t-butoxy-carbonyltyrosine triflate methyl ester). This compound is then condensed with an arylboronic acid (e.g. phenylboronic acid) in the presence of anhydrous potassium carbonate, and tetrakis (triphenylphosphine) palladium (O) complex as catalyst, in toluene preferably at an elevated temperature, advantageously at about 100° to obtain N-t-butoxycarbonyl-4-biphenylalanine methyl ester. After N-deacylation, substantially optically pure 4-biphenylalanine methyl ester is obtained with a configuration corresponding to that of the tyrosine derivative used as starting material.

The arylboronic acids are either commercial or can be prepared as described in the literature, e.g. J. Org. Chem. 49, 5237 (1984).

The preparation of the compounds of the invention according to process (b) involves the condensation of a protected tetrazole of formula V, with a reactive esterified derivative of $R_1$-hydroxymethylphosphonic acid of formula VI, e.g. dimethyl (trifluoromethylsulfonyloxy)-$R_1$-substituted-methylphosphonate in a polar solvent, such as methylene chloride, in the presence of a base, e.g. a tertiary amine such as diisopropylethylamine, at a temperature near room temperature. The resulting protected tetrazoles can be selectively deprotected to the free tetrazoles with a base, e.g. DBU in an inert solvent, such as methylene chloride.

The starting materials of formula VI may be prepared by treatment of an aldehyde $R_1$—CHO, wherein $R_1$ has meaning as defined hereinabove, with a compound of formula IVb

wherein $R_b$ and $R_b'$ have meaning as defined above, e.g. dibenzyl phosphite, in the presence of base, e.g. potassium fluoride or DBU and conversion of the resulting product to a compound of formula VI wherein Z is e.g. trifluoromethylsulfonyloxy by treatment with triflic anhydride or trifluoromethylsulfonyl chloride in the presence of base, e.g. 2,6-lutidine at low temperature (e.g. −50° C.).

The preparation of the compounds of the invention according to process (c) can be carried out according to methodology for tetrazole ring formation as described under process (a) above for the preparation of tetrazole intermediates of formula V.

The starting amides of formula VII can be prepared by condensation of the respective carboxylic acids or esters with an amine of formula XII.

The carboxylic acids can in turn be obtained from esters thereof which can be prepared according to process (a) above, except that compounds represented by formula III are replaced by compounds of formula IIIa

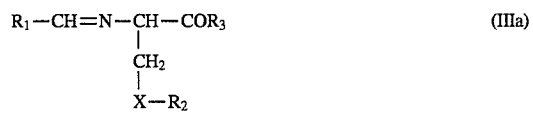

wherein X and $R_2$ have meaning as defined above and $COR_3$ represents esterified carboxyl.

Alternately, the carboxylic acids can be prepared by condensing under reductive amination conditions a compound of the formula XIII

wherein $R_b$ and $R_b'$ represent lower alkyl or aryl-lower alkyl, with a compound of formula XIV $$R_2—X—CH_2CO—COR_3 \qquad (XIV)$$

wherein $R_2$ and X have meanings as defined hereinabove, and $COR_3$ represents esterified carboxyl, such as lower alkoxycarbonyl.

The preparation involves the reductive amination of the appropriate pyruvic acid or derivative thereof of formula XIV with a diester of $R_1$-substituted aminomethylphosphonic acid of formula XIII (e.g. the dimethyl ester), in the presence of a reducing agent such as hydrogen or sodium cyanoborohydride under standard reductive amination conditions, to obtain compounds of formula XV

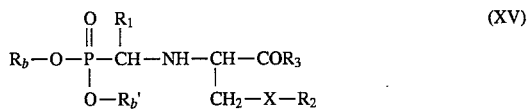

wherein $R_1$, $R_2$, X, $R_b$, and $R_b'$ have meaning as defined above, and $COR_3$ represents esterified carboxy. The amino protecting group $R_p'$ can be introduced according to methods well-known in the art.

The $R_1$-substituted aminomethylphosphonic acid diesters of formula XIII are prepared according to methods known in the art, for instance as described in Tetrehedron Letters 6827 (1990) and Phosphorus and Sulfur 32, 119 (1987).

As to the pyruvic acid esters of formula XIV, such are known in the art or are in turn prepared by methods analogous to those used for the preparation of substituted pyruvic acids, e.g. by condensation of e.g. the methyl ester of a biarylacetic acid with diethyl oxalate in the presence of a base, e.g. potassium t-butoxide, followed by hydrolyric decarboxylation.

The preparation of the compounds of the invention according to process (d) can be carried out according to procedures known in the art for the preparation of tetrazoles from nitriles e.g. as described in J. Am. Chem. Soc. 80, 3908 (1958) and J. Org. Chem. 56, 2395 (1991).

Hydrazoic acid is preferably generated from ammonium chloride/sodium azide in situ.

The starting nitriles can be prepared in a conventional manner by dehydration of the corresponding primary amides which can in turn be obtained from the carboxylic acid esters, described under process (c), by treatment with ammonia.

If a trialkylsilyl azide (such trimethylsilyl azide) or a trialkyltin azide is used, the resulting tetrazole may be substituted by trialkyltin or trialkylsilyl. Such groups may be removed by hydrolysis, e.g. with dilute acid.

The conversion according to process (e) of phosphonate esters obtained in the above processes, e.g. of formula X wherein $R_a$, and $R_a'$, represent lower alkyl or aryl-lower alkyl, to phosphonic acids of formula I can be carried out using known reagents for converting phosphonic acid esters to phosphonic acids, e.g. hydrobromic acid in glacial acetic acid, trimethylsilyl bromide, or by catalytic hydrogenation when such represent optionally substituted benzyl.

The compounds of the invention so obtained, can be converted into each other according to conventional methods. Thus, any resulting free acid can be converted into a corresponding metal, ammonium or acid addition salt respectively, by reacting it with an equivalent amount of the corresponding base, e.g. said free acids with alkali or ammonium hydroxides or carbonates. Any resulting salt may also be converted into the free compound, by liberating the latter with stronger acids. In view of the close relationship between the free compounds and the salts thereof, whenever a compound of the invention, or intermediate, is referred to in this context, a corresponding salt is also intended, provided such is possible or appropriate under the circumstances.

The compounds, including their salts, may also be obtained in the form of their hydrates, or include other solvents used for the crystallization.

Furthermore, the functional derivatives of the free acids of formula I, wherein the phosphono hydroxyl groups are esterified by identical or different radicals may be prepared by condensing a free phosphonic acid of formula I or a mono-ester derivative thereof with an esterifying agent of the formula XVI

wherein Z represents hydroxy or a reactive esterified hydroxyl group; and $R_7$ represents an esterifying radical as defined herein for the phosphonyl esters (e.g. R and R').

The esterification of the phosphonyl group, with a compound of formula XVI wherein Z represents a reactive esterified hydroxyl group, is performed in a manner known per se, in the presence of for example an organic base, such as an organic amine, for example a tertiary amine, such as tri-lower alkylamine, for example trimethylamine, triethylamine or ethyl-di-isopropylamine, an N,N-di-lower-alkylaniline, for example N,N-di-methylaniline, or a quaternary ammonium base, such as a tetraalkylammonium hydroxide, carbonate or hydrogen carbonate, for example in which alkyl is e.g. methyl, ethyl, propyl, isopropyl, butyl, or the like, or an alkali metal salt of bis-trialkylsilylamide (e.g. trimethyl) optionally in the presence of a crown ether such as 18-crown-6 in a suitable inert solvent or solvent mixture, e.g. acetonitrile, toluene, and the like.

The compounds of formula XVI are known or can be prepared by methods well-known to the art.

A compound of the formula XVI wherein Z is a reactive esterified hydroxyl group can be prepared in situ. For example, a compound of the formula XVI wherein Z is chloro can be converted by treatment with sodium iodide in a solvent, for example in acetone or acetonitrile, into a compound of the formula XVI wherein Z is iodo; or esterification can be carried out with a chloro compound of the formula XVI in the presence of sodium iodide.

Esters of the invention (phosphonic acid di-esters), can be converted to compounds of the invention with one or two free phosphonyl hydroxy groups using methods and conditions generally known in the art and illustrated herein. Depending on type of ester involved, useful reagents include aqueous acids or bases; also anhydrous reagents such as trialkylsilyl halides, hydrobromic acid in glacial acetic acid; also hydrogen and a hydrogenolysis catalyst. For instance, dialkyl esters can be converted to the free phosphonic acids by treatment with hydrobromic acid in glacial acetic acid, e.g. at room temperature or elevated temperature.

Any benzyl esters can be selectively hydrogenolyzed with e.g. hydrogen in the presence of a catalyst such as palladium on charcoal, or treated with e.g. trimethylsilyl bromide to obtain the free phosphonic acids.

Phosphono diesters wherein the esterifying groups (R and R') represent α-acyloxyalkyl can be converted to corresponding phosphono monoesters (wherein one of R and R' represents hydrogen) by treatment with one molar equivalent of an aqueous base, e.g. 1N sodium hydroxide.

Phosphono diesters wherein the esterifying groups (e.g. R and R' in formula II) represent aryl can advantageously be converted to the corresponding phosphono monoesters (wherein one of R and R' represents hydrogen) using dilute aqueous acid (e.g. dilute hydrochloric acid) in a polar water miscible solvent such as acetonitrile.

Furthermore, phosphono diesters wherein the esterifying groups represent aryl can first be converted to the corresponding phosphono diesters wherein the esterifying groups represent e.g. methyl, by treatment with methanol in the presence of potassium fluoride and a crown ether such as 18-crown-6. Subsequent treatment with hydrobromic acid in glacial acetic acid yields the free phosphonic acid.

In the case mixtures of stereoisomers or optical isomers of the above compounds are obtained, these can be separated into the single isomers by methods in themselves known, e.g., by fractional distillation, crystallization and/or chromatography and racemic products can be resolved into the optical antipodes.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres; at low temperatures, room temperature or elevated temperatures, preferably near the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The present invention additionally relates to the use in mammals of the compounds of the invention and their pharmaceutically acceptable, non-toxic acid addition salts, or pharmaceutical compositions thereof, as medicaments, for instance as endothelin-converting enzyme inhibitors, for the treatment of endothelin dependent disorders, e.g. cardiovascular disorders such as hypertension, heart failure and cerebral ischemia.

The present invention also relates to the use of the compounds of the invention for the preparation of pharmaceutical compositions especially pharmaceutical compositions having endothelin-converting enzyme inhibiting activity.

The pharmaceutical compositions according to the invention are those suitable for enteral, such as oral or rectal, transdermal and parenteral administration to mammals, including man, for the treatment of endothelin-converting enzyme dependent disorders, comprising an effective amount of a pharmacologically active compound of the invention or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous careers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 5 and 100 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Optical rotations are measured at room temperature at 589 nm (D line of sodium).

The prefixes R and S are used to indicate the absolute configuration at each asymmetric center and the corresponding enantiomers.

The tetrazole derivatives are named as 1-H or 1-substituted compounds. However, such may exist as tautomeric 2-H or 2-substituted compounds or as a mixture of said tautomeric forms.

The abbreviation min represents minutes(s) and the abbreviation hr(s) represents hour(s).

The diastereomers with (S) configuration at the asymmetric carbon atom adjacent to the tetrazole ring and undetermined configuration at the carbon atom adjacent to the phosphono grouping are designated A and B, respectively.

EXAMPLE 1

(a) To a solution of {1-[2-(S)-biphenyl-4-yl-1-(1H-tetrazol-5-yl)-ethylamino]-3-(naphthalen-1-yl)-propyl}-phosphonic acid dibenzyl ester (diastereomer A) (0.1 g, 0.144 mmol) in methylene chloride (1 mL) cooled to 0° C. under nitrogen is added bromotrimethylsilane (0.11 mL, 0.86 mmol). The reaction mixture is stirred and allowed to warm up to room temperature. After 45 min, the solvent is evaporated in vacuo and the residue is dissolved in ethyl acetate (10 mL). Water (10 mL) is added along with a few drops of HCl 0.1N and the product is allowed precipitate slowly. The solid is filtered and dried under high vacuum at 60° C. for 5 hours to give {1-[2-(S)-biphenyl-4-yl-1-(1H-tetrazol-5-yl)-ethylamino]-3-(naphthalen-1-yl)-propyl}-phosphonic acid (diastereomer A), m.p. 218°–221° C.; $^1$H NMR (300 MHz, DMSO $d_6$/TFA) δ 1.88–2.00 (m, 1H), 2.14–2.18 (m, 1H), 2.96–3.04 (m, 2H), 3.18–3.28 (m, 1H), 3.32–3.40 (m, 1H), 3.67 (dd, J=4.0, 13.0 Hz, 1H), 5.38 (dd, J=4.2, 11 Hz, 1H), 7.09 (d, J=8.2 Hz, 2H), 7.21 (d, J=6.8 Hz, 1H), 7.30–7.59 (m, 12H), 7.76, (d, J=8.2 Hz, 1H), 7.90 (dd, J=2, 7.3 Hz, 1H), 8.08 (d, J=7.3 Hz, 1H);

(b) Similarly prepared is {1-[2-(S)-biphenyl-4-yl-1-(1H-tetrazol-5-yl)-ethylamino]-3-(naphthalen-1-yl)-propyl}phosphonic acid (diastereomer B), m.p. 200°–202° C.; $^1$H NMR (300 MHz, DMSO $d_6$/TFA) δ 2.04–2.19 (m, 2H), 3.16 (dd, J=5.5, 12.5 Hz, 1H), 3.35 (dd, J=4, 12.5 Hz, 1H), 3.46 (t, J=12 Hz, 1H), 3.61–3.70 (m, 1H), 3.75 (dd, J=4, 12 Hz, 1H), 5.37 (dd, J=4, 11 Hz, 1H), 7.15 (d, J=8.2 Hz, 2H), 7.30–7.46 (m, 6H), 7.50–7.59 (m, 6H), 7.78 (d, J=8 Hz, 1H), 7.92 (d, J=8 Hz, 1H), 8.15 (d, J=8 Hz, 1H); $^{31}$P NMR (121.5 MHz, DMSO $d_6$/TFA) δ 16.21.

Diastereoisomer A is the more active ECE inhibitor.

The starting materials are synthesized as follows:

To a stirred solution of 3-(naphthalen-1-yl)propanal (2.3 g, 12.5 mmol) in DMF (6 mL) under nitrogen is added dibenzyl phosphite (3.3 g, 12.5 mmol), followed by potassium fluoride (0.94 g, 16.2 mmol). After 2 hours, the stirred suspension is diluted with ethyl acetate (60 mL) and washed with water (3×20 mL). The organic layer is dried over anhydrous $MgSO_4$, filtered and concentrated in vacuo. The residue is purified by flash-chromatography on silica gel, eluting with a gradient of ethyl acetate in hexane (30% to 40% ). Concentration of the pure fractions in vacuo yields [1-hydroxy-3-(naphthalen-1-yl)-propyl]phosphonic acid dibenzyl ester as an oil which solidifies on standing.

$^1$H NMR (300 MHz, $CDCl_3$) δ 2.05–2.24 (m, 2H), 3.10–3.18 (m, 1H), 3.38–3.43 (m, 1H), 3.95–4.01 (m, 2H), 4.97–5.14 (m, 4H), 7.23–7.41 (m, 12H), 7.45–5.53 (m, 2H), 7.72 (d, J=8 Hz, 1H), 7.84–7.87 (m, 1H), 8.00–8.05 (m, 1H); $^{31}$P NMR (121.5 MHz, $CDCl_3$) δ 26.61.

A solution of [1-hydroxy-3-naphthalen-1-yl-propyl]-phosphonic acid dibenzyl ester (3.3 g, 7.89 mmol) in methylene chloride (35 mL) under nitrogen is cooled to −50° C. 2,6-Lutidine (1.03 mL, 8.87 mmol) is added, followed by trifluoromethanesulfonic anhydride (1.43 mL, 8.5 mmol) over 8 min. The reaction mixture is stirred for 1 hour, then partitioned between cold ether (100 mL) and cold water (100 mL). The organic layer is washed once with cold 1N HCl and cold brine, then dried over $MgSO_4$, filtered and concentrated under vacuum at room temperature to give [1-(trifluoromethanesulfonyloxy)-3-(naphthalen-1-yl)-propyl] phosphonic acid dibenzyl ester as a yellow oil: $^{31}$P NMR (121.5 MHz, $CDCl_3$) δ 16.58.

{1-[2-(S)-biphenyl-4-yl-1-(1-(2-cyanoethyl)-1H-tetrazol-5-yl)-ethylamino]-3-(naphthalen-1-yl)-propyl}phosphonic acid dibenzyl ester (diastereomers A and B) are prepared as follows:

(i) Triflate method: To a solution of (S)-3-[5-(1-amino-2-biphenyl-4-yl-ethyl)tetrazol-1-yl]-propionitrile (U.S. Pat. No. 5,273,990, 1.43 g, 3.31 mmol) in methylene chloride (8 mL) under nitrogen is added a solution of [1-(trifluoromethanesulfonyloxy)-3-(naphthalen-1-yl)-propyl]phosphonic acid dibenzyl ester (3.83 g, 6.62 mmol) in methylene chloride (6 mL), followed by diisopropylethyl amine (0.51 mL, 3.64 mmol). The reaction mixture is stirred for 72 hrs and concentrated. Purification by flash-chromatography on silica gel, eluting with 40% ethyl acetate in hexane leads to the separation of the 2 diastereomers A and B.

(ii) Imine method: To a solution of (S)-3-[5-(1-amino-2-biphenyl-4-yl-ethyl)tetrazol-1-yl]-propionitrile (1 g, 2.31 mmol) in methylene chloride (3 mL) is added a solution of 3-(1-(naphthalen-1-yl)propanal (0.43 g, 2.31 mmol) in methylene chloride (0.5 mL), followed by anhydrous MgSO₄ (1.11 g). The mixture is mechanically stirred for 2.5 hours, diluted with methylene chloride (10 mL), filtered and concentrated in vacuo to give the crude imine intermediate. Meanwhile, a solution of dibenzyl phosphite (0.46 mL, 2.08 mmol) in methylene chloride (6 mL) is cooled under nitrogen to 0° C., treated successively with triethylamine (0.34 mL, 2.42 mmol) and chlorotrimethylsilane (0.31 mL, 2.42 mmol), and stirred for 1 hour. To this cold mixture is added a solution of the crude imine prepared above in methylene chloride (2 mL). The reaction mixture is allowed to warm up to room temperature and stirred for 18 hours. Water (10 mL) is added and the organic layer is separated, dried over MgSO₄, filtered and concentrated. The oily residue is purified by flash-chromatography as described above to afford each of the two diastereomers A and B.

¹H NMR (300 MHz, CDCl₃) for Isomer A: δ 1.80–2.00 (m, 1H), 2.10–2.30 (m, 2H), 2.50–2.60 (m, 2H), 2.90–3.50 (m, 4H), 3.90–4.15 (m, 2H), 4.65–5.05 (m, 6H), 6.90–7.00 (m, 2H), 7.00–7.10 (m, 2H), 7.20–7.50 (m, 19H), 7.60–7.70 (m, 1H), 7.80–7.90 (m, 2H).

¹H NMR (300 MHz, CDCl₃) for Isomer B: δ 1.79–2.06 (m, 2H), 2.18–2.26 (m, 1H), 2.42–2.53 (m, 1H), 2.68–2.79 (m, 1H), 2.93–3.03 (m, 2H), 3.10–3.36 (m, 3H), 4.16–4.35 (m, 2H), 4.55–4.60 (m, 1H), 4.77–4.99 (m, 4H), 7.07 (d, J=7.8 Hz, 2H), 7.17 (d, J=7 Hz, 1H), 7.25–7.56 (m, 20H), 7.74 (d, J=8.2 Hz, 1H), 7.86–7.92 (m, 2H).

³¹P NMR (121.5 MHz, CDCl₃) δ for isomer A: 27.17, for isomer B: 27.2.

To a solution of {1-[2-(S)-biphenyl-4-yl-1-(1-(2-cyanoethyl)-1H-tetrazol-5-yl)-ethylamino]-3-(naphthalen-1-yl-propyl}-phosphonic acid dibenzyl ester diastereomer A (190.4 mg, 0.25 mmol) in methanol (0.6 mL) and THF (0.4 mL) under nitrogen is added NaOH 1N (0.31 mL). After 2 hours, the mixture is acidified with 1N HCl to pH 1 and partitioned between ethyl acetate (10 mL) and water (10 mL). The organic layer is dried over anhydrous MgSO₄, filtered and concentrated. The oily residue is purified by flash-chromatography on silica gel, eluting with 5% methanol in methylene chloride to give {1-[2-(S)-biphenyl-4-yl-1-(1H-tetrazol-5-yl)-ethylamino]-3-(naphthalen-1-yl)-propyl}-phosphonic acid dibenzyl ester (diastereomer A) as a foam; ³¹P NMR (121.5 MHz, CDCl₃) δ 26.92. The corresponding diastereomer B is similarly prepared from the diastereomer B intermediate.

EXAMPLE 2

The following compounds are prepared similarly:

(a) {1-[2-(S)-biphenyl-4-yl-1-(1H-tetrazol-5-yl)-ethylamino]-3-(phenyl)propyl}-phosphonic acid (diastereomer A). m.p. 198°–202° C.; ¹H NMR (300 MHz, DMSO d₆) δ 1.60–1.75 (m, 1H), 1.80–2.00 (m, 1H), 2.30–2.36 (m, 1H), 2.50–2.53 (m, 1H), 3.23 (t, J=12 Hz, 1H), 3.36 (br d, J=10 Hz, 1H), 5.08 (br s, 1H), 6.99 (d, J=7.2 Hz, 2H), 7.08 (d, J=8.1 Hz, 2H), 7.12 (t, J=7.3 Hz, 1H), 7.20 (t, J=7.3 Hz, 2H), 7.32 (t, J=7.3 Hz, 1H), 7.41 (t, J=7.5 Hz, 2H), 7.48 (d, J=8.1 Hz, 2H), 7.57 (d, J=7.5 Hz, 2H); ³¹P NMR (121.5 MHz, DMSO d₆) δ 21.25

(b) {1-[2-(S)-biphenyl-4-yl-1-(1H-tetrazol-5-yl)-ethyl(b){1-(2-(S)-biphenyl-4-yl-1-(1H-tetrazol-5-yl)-ethylamino]-3-(phenyl)-propyl}-phosphonic acid (diastereomer B), m.p. 152°–156° C.; ¹H NMR (300 MHz, DMSO d6/TFA) d 1.75–2.14 (m, 2H), 2.52–2.77 (m, 2H), 3.17 (dt, J=6, 14 Hz, 1H), 3.34–3.42 (m, 1H), 3.50 (dd, J=5, 13 Hz, 1H), 5.10 (dd, J=5.5, 9 Hz, 1H), 7.09–7.35 (m, 8H), 7.42 (t, J=7.5 Hz, 2H), 7.53 (d, J=8 Hz, 2H), 7.59 (d, J=8 Hz, 2H); ³¹P NMR (121.5 MHz, DMSO d₆ δ 18.88.

(c) {1-[2-(S)-biphenyl-4-yl-1-(1H-tetrazol-5-yl)-ethylamino]-3-(3-pyridyl)propyl}phosphonic acid.

(d) {1-[2-(S)-biphenyl-4-yl-1-(1H-tetrazol-5-yl)-ethylamino]-3-(3-isoquinolinyl)propyl}phosphonic acid.

(e) {1-[2-(S)-biphenyl-4-yl-1-(1H-tetrazol-5-yl)-ethylamino]-3-(naphthalen-2-yl)propyl}phosphonic acid.

What is claimed is:

1. A compound of formula I

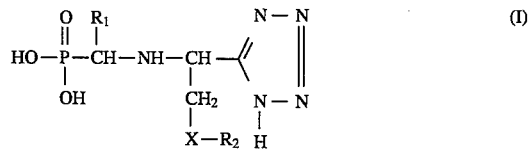

or a tautomer thereof wherein R₁ is (carbocyclic or heterocyclic) aryl-C₁–C₄-alkyl; X is phenylene, phenylene substituted by lower alkoxy, lower-alkyl, halogen or trifluoromethyl, or X is ethynylene; R₂ is carbocyclic or heterocyclic aryl; and heterocyclic aryl in the above definitions represents furanyl or furanyl substituted by lower alkyl, pyridyl or pyridyl substituted by lower alkyl, halogen or cyano, thienyl or thienyl substituted by lower alkyl, pyrrolyl or pyrrolyl substituted by lower alkyl, isoxazolyl or isoxazolyl substituted by lower alkyl, triazolyl or triazolyl substituted by lower alkyl, tetrazolyl, indolyl, or indolyl substituted by lower alkyl, lower alkoxy or hydroxy, benzofuranyl or benzofuranyl substituted by lower alkyl, hydroxy or lower alkoxy, benzothienyl or benzothienyl substituted by lower alkyl, hydroxy or lower alkoxy, benzoxazolyl or benzoxazolyl substituted by lower alkyl, hydroxy or lower alkoxy, quinolinyl or quinolinyl substituted by lower alkyl, or isoquinolinyl or isoquinolinyl substituted by lower alkyl a pharmaceutically acceptable mono- or di-ester derivative thereof in which one or both of the acidic hydroxy groups of the phosphono functional group are esterified in form of a pharmaceutically acceptable mono- or di-ester, or a pharmaceutically acceptable salt thereof.

2. A compound according to claim 1 wherein R₁ is carbocyclic aryl-C₁–C₄-alkyl.

3. A compound according to claim 1 wherein R₁ is heterocyclic aryl-C₁–C₄-alkyl.

4. A compound according to claim 1 wherein R¹ is naphthyl-C₁–C₄-alkyl optionally substituted by lower alkyl, lower alkoxy or halogen.

5. A compound according claim 1 wherein X is phenylene.

6. A compound according to claim 5 wherein R₂ is monocylic carbocyclic aryl.

7. A compound according to claim 4 wherein R₂ is phenyl.

8. A compound of formula II

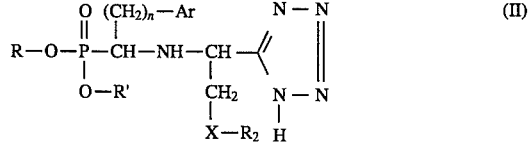

or a tautomer thereof wherein R and R' represent independently hydrogen, carbocyclic aryl, 6-tetrahydronaphthyl, 5-indanyl, α-(trichloromethyl, carboxyl, esterified carboxyl or amidated carboxyl)-substituted-(lower alkyl or aryl-lower alkyl), acyloxymethyl optionally monosubstituted on methyl carbon by lower alkyl, by C₅–C₇-cycloalkyl, by aryl or by aryl-lower alkyl; Ar represents phenyl, or phenyl substituted by hydroxy, lower alkyl, lower alkoxy, halogen or trifluoromethyl; or Ar represents naphthyl, indolyl, benzofuranyl, benzothienyl, quinolinyl, isoquinolinyl or benzoxazolyl, each optionally substituted by hydroxy, lower alkyl or lower alkoxy; n represents the integer 1, 2 or 3; X represents phenylene or ethynylene; $R_2$ represents naphthyl, phenyl or phenyl substituted by lower alkyl or lower alkoxy; or $R_2$ represents pyridyl, thienyl, furanyl, isoxazolyl, triazolyl, tetrazolyl or pyrrolyl each unsubstituted or substituted by lower alkyl; or a pharmaceutically acceptable salt thereof.

9. A compound according to claim 8 wherein R and R' independently represent hydrogen, α-(carboxy, lower alkoxycarbonyl, carbocyclic arylmethoxycarbonyl, aminocarbonyl or mono- or di-lower alkylamino-carbonyl)-substituted-(lower alkyl or carbocyclic aryl-lower alkyl), 5-indanyl, phenyl, or phenyl substituted by one, two or three substituents selected from lower alkyl, halogen, lower alkoxy, lower alkanoylamino, trifluoromethyl, lower alkyl-(thio, sulfinyl or sulfonyl), and lower alkoxycarbonyl.

10. A compound according to claim 8 wherein R and R' are either identical, or one of R and R' represents hydrogen while the other of R and R' has any of the other meanings as defined in said claim.

11. A compound according to claim 8 having the (S)-configuration at the asymmetric carbon adjacent to the tetrazole ring.

12. A compound according to claim 1 of formula I wherein $R_1$ represents 1-naphthyl-($C_1$–$C_4$)-alkyl, X represents 1,4-phenylene and $R_2$ represents phenyl; the S,S or R,S diastereomer thereof; a pharmaceutically acceptable salt thereof; or a prodrug ester thereof.

13. A compound according to claim 8 of formula II wherein n represents 1, 2 or 3; Ar represents 1-naphthyl; X represents 1,4-phenylene; $R_2$ represents phenyl; R and R' represent hydrogen or phenyl; the S,S or R,S-diastereomer thereof; or a pharmaceutically acceptable salt thereof; or a prodrug ester thereof.

14. A compound according to claim 10 being {1-[2-(S)-biphenyl-4-yl-1-(1H-tetrazol-5-yl)-ethylamino]-3-(1-naphthyl)-propyl}-phosphonic acid, a diastereomer thereof or a prodrug ester thereof.

15. A compound according to claim 14 which is the higher melting diastereomer, a pharmaceutically acceptable salt thereof or a prodrug ester thereof.

16. An endothelin converting enzyme pharmaceutical composition comprising an effective endothelin converting enzyme inhibiting amount of a compound of claim 1 in combination with one or more pharmaceutically acceptable carriers.

17. A method of inhibiting endothelin converting enzyme in mammals which comprises administering to a mammal in need thereof an effective endothelin converting enzyme inhibiting amount of a compound of claim 1.

18. A method of inhibiting the formation of endothelin in mammals which comprises administering to a mammal in need thereof an effective endothelin converting enzyme inhibiting amount of a compound of claim 1.

19. A method of treating endothelin dependent disorders in mammals which comprises administering to a mammal in need thereof an effective endothelin converting enzyme inhibiting amount of a compound of claim 1.

20. A method according to claim 19 of treating cardiovascular disorders.

\* \* \* \* \*